US009771309B2

(12) United States Patent
Sharratt et al.

(10) Patent No.: US 9,771,309 B2
(45) Date of Patent: Sep. 26, 2017

(54) CHROMIA BASED FLUORINATION CATALYST

(75) Inventors: Andrew P Sharratt, Cheshire (GB); John D Scott, Shropshire (GB)

(73) Assignee: MEXICHEM AMANCO HOLDING S.A. DE C.V., Tlalnepantla (MX)

( * ) Notice: Subject to any disclaimer, the term of this patent is extended or adjusted under 35 U.S.C. 154(b) by 1264 days.

(21) Appl. No.: 11/887,972

(22) PCT Filed: Apr. 10, 2006

(86) PCT No.: PCT/GB2006/001291
§ 371 (c)(1),
(2), (4) Date: Feb. 11, 2009

(87) PCT Pub. No.: WO2006/106353
PCT Pub. Date: Oct. 12, 2006

(65) Prior Publication Data
US 2009/0209792 A1 Aug. 20, 2009

(30) Foreign Application Priority Data

Apr. 8, 2005 (GB) .................................. 0507139.4

(51) Int. Cl.
| | | |
|---|---|---|
| *B01J 21/00* | (2006.01) | |
| *B01J 23/00* | (2006.01) | |
| *B01J 25/00* | (2006.01) | |
| *B01J 29/00* | (2006.01) | |
| *C07C 17/20* | (2006.01) | |
| *B01J 23/26* | (2006.01) | |
| *C07C 17/21* | (2006.01) | |

(52) U.S. Cl.
CPC ............. *C07C 17/206* (2013.01); *B01J 23/26* (2013.01); *C07C 17/21* (2013.01)

(58) Field of Classification Search
USPC .......... 502/305–307, 256, 100, 300
See application file for complete search history.

(56) References Cited

U.S. PATENT DOCUMENTS

| | | | |
|---|---|---|---|
| 3,235,612 A | 2/1966 | Anello | |
| 3,755,477 A | 8/1973 | Firth et al. | |
| 4,158,675 A | 6/1979 | Potter | |
| 5,155,082 A | 10/1992 | Tung et al. | |
| 5,334,786 A | 8/1994 | Koyama et al. | |
| 5,354,927 A | 10/1994 | Carmello et al. | |
| 5,475,168 A | 12/1995 | Masiero et al. | |
| 5,523,500 A | 6/1996 | Cheminal et al. | |
| 5,545,778 A * | 8/1996 | Tung ....................... C07C 17/21 570/165 |
| 5,563,305 A | 10/1996 | Masiero et al. | |
| 5,659,094 A | 8/1997 | Kim et al. | |
| 5,672,789 A | 9/1997 | Kim et al. | |
| 5,744,660 A * | 4/1998 | Bradley ................ C07C 17/206 570/151 |
| 5,773,671 A | 6/1998 | Tung | |
| 5,849,963 A | 12/1998 | Homoto et al. | |
| 6,028,026 A | 2/2000 | Rao et al. | |
| 6,034,289 A | 3/2000 | Christoph et al. | |
| 6,172,270 B1 | 1/2001 | Tatematsu | |
| 6,242,659 B1 | 6/2001 | Requieme et al. | |
| 6,274,780 B1 | 8/2001 | Rao et al. | |
| 6,359,183 B1 | 3/2002 | Christoph et al. | |
| 6,403,524 B2 * | 6/2002 | Scott ....................... B01J 23/26 502/305 |
| 6,433,233 B1 | 8/2002 | Kanemura et al. | |
| 2004/0049088 A1 | 3/2004 | Lacroix et al. | |
| 2005/0227865 A1 * | 10/2005 | Nappa ..................... B01J 23/26 502/319 |

FOREIGN PATENT DOCUMENTS

| | | |
|---|---|---|
| CN | 1109801 | 10/1995 |
| EP | 0502605 | 9/1992 |
| EP | 0537760 | 4/1993 |
| EP | 0548742 | 6/1993 |
| EP | 0569832 | 11/1993 |
| EP | 0610963 | 8/1994 |
| EP | 0641598 | 3/1995 |
| EP | 0657408 | 6/1995 |
| EP | 0657409 | 6/1995 |
| EP | 0773061 | 5/1997 |
| EP | 0955088 | 10/1999 |
| EP | 0957074 | 11/1999 |

(Continued)

OTHER PUBLICATIONS

Brunet et al., Characterization by Temperature-Programmed Reduction and by Temperature-Programmed Oxidation (TPR-TPO) of Chromium (III) Oxide-Based Catalysts: Correlation with the Catalytic Activity for Hydrofluoroalkane Synthesis, Journal of Catalysis 152, 70-74 (1995).
Adamczyk et al., Magnesium- and iron-doped chromium fluoride/hydroxyfluoride: synthesis, characterization and catalytic activity, J. Mater. Chem., 6(10), 1731-1735 (1996).
Birken et al., Etude en spectroscopie d'absorption X de catalyseurs de fluoration a base de chrome, Journal de Physique IV, Colloque C4, supplement au Journal de Physique III, vol. 6, C4-571-C3-579 (1996) English Abstract.
Bechadergue et al., Isomerization and Dismutation of Chlorofluoroethanes on a Cr2O3/C Catalyst, Applied Catalysis, 20, 179-187 (1986).
Marangoni et al., Catalyst for Fluorination of organic cholorocompounds, La Chimica E L'Industria, vol. 64 Pt 3, 135-140 (1982).
Cavani, F., et al., Chemical and Physical Characterization of Alumina-Supported Chromia-Based Catalysts and Their Activity in Dehydrogenation of Isobutane, Journal of Catalysis, 158(1), 1996, 236-250.

(Continued)

*Primary Examiner* — James McDonough
(74) *Attorney, Agent, or Firm* — Ryan Kromholz & Manion, S.C.

(57) ABSTRACT

A chromia-based fluorination catalyst comprising at least one additional metal selected from zinc, nickel, aluminum and magnesium in which from 0.1 to 8.0% by weight of the catalyst is in the form of one or more crystalline compounds of chromium and/or one or more crystalline compounds of the at least one additional metal. The catalyst can be used in processes for producing a fluorinated hydrocarbon.

10 Claims, No Drawings

(56) References Cited

FOREIGN PATENT DOCUMENTS

| | | | |
|---|---|---|---|
| EP | 957074 A1 * | 11/1999 | ............ C07C 17/20 |
| EP | 1038858 | 9/2000 | |
| EP | 1148039 | 10/2001 | |
| GB | 999444 | 7/1965 | |
| GB | 2030981 | 4/1980 | |
| GB | 1589924 | 5/1981 | |
| JP | 57197232 | 12/1982 | |
| JP | 57197233 | 12/1982 | |
| JP | 02111733 | 4/1990 | |
| JP | 03058946 | 3/1991 | |
| JP | 08038904 | 2/1996 | |
| JP | 08108073 | 4/1996 | |
| JP | 09067278 | 3/1997 | |
| KR | 9610776 | 8/1996 | |
| WO | 93/08146 | 4/1993 | |
| WO | 94/06558 | 3/1994 | |
| WO | 95/27688 | 10/1995 | |
| WO | 96/41679 | 12/1996 | |
| WO | 97/10053 | 3/1997 | |
| WO | 98/10862 | 3/1998 | |
| WO | WO 9810862 A1 * | 3/1998 | ............ B01J 23/26 |
| WO | 98/47841 | 10/1998 | |
| WO | 00/21660 | 4/2000 | |
| WO | 01/74483 | 10/2001 | |
| WO | 2004/018093 | 3/2004 | |
| WO | 2004/018095 | 3/2004 | |

OTHER PUBLICATIONS

Cho D., et al., Catalytic fluorination of 1,1,1-trifluoro-2-chloroethane (HCFC-133a) over chromium catalysts, Catalysis Letters, 43, 1998, 199-203.
Cho et al., Preparation and characterization of magnesia-supported chromium catalysts for the fluorination of 1,1,1-trifluoro-2-chloroethane (HCFC-133a), Applied Catalysis B: Environmental, 18, 1998, 251-261.
Brunet et al., Influence of the morphology and of the composition of chromium oxides on their catalytic activity for the gas phase fluorination of 1,1,1-trifluoro-2-chloro-ethane. Preparation of hydrofluorocarbons, Applied Catalysis A: General, 168, 1998, 57-61.
Notice of Allowance China Application No. 200680016007.6, dated Apr. 26, 2012.
Japanese Office Action for Japanese patent Application No. 2008-504852, dated Jun. 12, 2012 (English Translation).

* cited by examiner

CHROMIA BASED FLUORINATION CATALYST

This application claims benefit of PCT/GB2006/001291, filed Apr. 10, 2006.

The present invention relates to a fluorination catalyst and the production and use thereof.

Fluorination processes in which a starting material is reacted with hydrogen fluoride to introduce one or more fluorine atoms into the starting material are well known and widely used by industry. Such processes may take place in the liquid or vapour phase, although the vapour phase is more widely used. Catalysts suitable for use in these processes include those comprising or based on chromia. Several catalysts for use in fluorination reactions have been described in the prior art.

Many previously described catalysts are amorphous. These catalysts may optionally contain a metal in addition to chromium. For example, EP-A-0502605 describes chromium-containing fluorination catalysts that contain an activity-promoting amount of zinc or a compound of zinc. EP-A-0773061 describes catalysts based on amorphous chromium oxide that may contain an additional metal such as zinc or manganese. EP-A-0957074 describes a fluorination process using a catalyst comprising a compound oxide of chromium and at least one of zinc, zirconium and manganese in which the chromium oxide shows substantially no crystallizability characteristic before or during the fluorination reaction.

Chromia-based catalysts having some crystalline properties are known. For example, WO98/10862 describes chromia-based catalysts that comprise an activity promoting amount of zinc or a compound of zinc which have an apparent degree of crystallinity as represented by alpha chromia type crystals of greater than 8%, more preferably greater than 20% and less than 50% by weight. Such catalysts were found to be more chemically robust when compared to amorphous equivalents. However, a significant problem associated with the use of the catalysts described in WO98/10862 is that they lack the physical robustness associated with amorphous chromia based catalysts and are difficult to handle in practice.

A significant problem experienced with many fluorination reactions is that a number of undesirable by-products may be produced in addition to the desired product. These by-products can often be difficult to remove from the desired product, for example because they form azetropes or near azeotropes with the desired product. One process that is of particular commercial interest is the production of pentafluoroethane (R125) from perchloroethylene. A number of undesirable by-products are typically produced during this reaction. These by-products include those of the generic formula $C_2Cl_{6-x}F_x$, where x is 0 to 6 (the 110 series) and those of the generic formula $C_2H_2Cl_{4-x}F_x$, where x is 0 to 4 (the 130 series). Impurities of both the 110 series and the 130 series may be produced by disproportionation of 120 series compounds (ie those of the generic formula $C_2HCl_{5-x}F_x$, where x is 0 to 5). Under the conditions at which many known methods for preparing R125 are conducted, the 110 and 130 series products may then fluorinate to produce further impurities. Examples of 110 series impurities include 1,1,2,2-tetrachloro-1,2-difluoroethane (R112) and 1,1,1,2-tetrachloro-2,2-difluoroethane (R112a), which may then be further fluorinated to produce chloropentafluoroethane (R115). R115 has high ozone depletion potential and, therefore, should only be present in R125 at low levels. This is particularly important in view of current environmental concerns about the ozone layer. R115 is, however, difficult to remove from R125 as it forms an azeotrope or a near azeotrope with R125 at most pressures.

This is just one example of a fluorination reaction and the undesirable by-products produced. It is well known in the art that undesirable by-products that may be difficult to remove from the desired product are produced in other fluorination reactions.

It is known from the prior art that catalysts that are suitable for use in addition reactions such as the addition of hydrogen fluoride to perchloroethylene are not particularly good catalysts for substitution reactions such as the substitution of chlorine atoms in dichlorotrifluoroethane ($CF_3CHCl_2$) (R-123) by fluorine atoms to produce chlorotetrafluoroethane ($CF_3CHClF$) (R-124) or pentafluoroethane ($CF_3CHF_2$) (R-125). As described in WO95/27688, it is often desirable to use one catalyst for the reaction of perchloroethylene with hydrogen fluoride to produce R-123 and a different catalyst to prepare R-124 or R-125 from R-123.

It is an object of the present invention to provide a catalyst that is suitable for use in both addition and substitution reactions.

The present inventors have surprisingly found that this object can be achieved by the use of a chromia-based fluorination catalyst comprising at least one additional metal selected from zinc, nickel, aluminium and magnesium, in which from 0.1 to 8.0% by weight of the catalyst is in the form of one or more crystalline compounds of chromium and/or one or more crystalline compounds of the at least one additional metal. Typically, from 0.1 to less than 8.0% by weight of the catalyst is in the form of one or more crystalline compounds of chromium and/or one or more crystalline compounds of the at least one additional metal, for example from 0.1 to about 7.5 or 7.8% by weight of the catalyst is in the form of one or more crystalline compounds of chromium and/or one or more crystalline compounds of the at least one additional metal.

The catalysts of the invention have a degree of crystallinity as defined above before use in an addition reaction and/or a substitution reaction. Preferably the catalysts have a degree of crystallinity of from 0.1 to 5% by weight, for example from 0.2 to 2.5% by weight and most preferably from 0.3 to 1.5% by weight of the catalyst. Suitable catalysts may contain for example about 0.4, 0.5, 0.6, 0.7, 0.8, 0.9, 1.0, 1.1, 1.2, 1.3 or 1.4% by weight of crystalline compounds of chromium, and/or crystalline compounds of the at least one additional metal before use in a substitution and/or addition reaction.

During use in an addition and/or substitution reaction the degree of crystallinity may change. Thus it is possible that a catalyst of the invention that has a degree of crystallinity as defined above before use in an addition or substitution reaction will have a degree of crystallinity outside these ranges during or after use in an addition or substitution reaction.

The metals in the catalyst are typically present in the form of metal oxides, oxyfluorides or fluorides. Thus, the crystalline material present in the catalysts of the invention is typically an oxide, oxyfluoride or fluoride of chromium and/or the at least one additional metal, such as crystalline chromium oxide.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (eg the graphite used in producing catalyst pellets) or more preferably by comparison of the intensity of the ED patterns of the sample materials with reference materials prepared from suitable internationally recognised standards, for example NIST (National Institute of Standards and Technology) reference materials.

The catalysts of the invention contain at least one additional metal selected from zinc, nickel, aluminium and magnesium and combinations thereof. The additional metal or metals may be present as the metal or as a compound of the metal. Preferably, the additional metal is zinc, alone or in combination with one of the other additional metals listed above, for example aluminium.

The total amount of the additional metal or metals present in the catalysts of the invention is typically from about 0.5% by weight to about 25% by weight, more preferably from about 1 to 10% by weight of the catalyst, still more preferably from about 3 to 8% by weight of the catalyst, for example about 4% by weight of the catalyst.

The preferred amount depends upon a number of factors such as the nature of the additional metal or metals and the nature of the chromium-containing catalyst, which is determined by a number of factors such as the way in which the catalyst is made.

It is to be understood that the amount of additional metal quoted herein refers to the amount of elemental metal whether present as elemental additional metal or as a metal compound.

The catalysts of the invention typically have a surface area of at least 50 $m^2/g$ and preferably from 70 to 250 $m^2/g$ and most preferably from 100 to 200 $m^2/g$ before it is subjected to pretreatment with a fluoride containing species such as hydrogen fluoride or a fluorinated hydrocarbon. During this pre-treatment, at least some of the oxygen atoms in the catalyst are replaced by fluorine atoms.

The catalysts of the invention preferably have a sulphate content of less than 10% w/w.

The catalysts of the invention typically have an advantageous balance of levels of activity and selectivity. Preferably, they also have a degree of chemical robustness that means that they have a relatively long working lifetime. It will be appreciated that the working life of a catalyst is very dependent on the reaction process in which it is used. For example, a catalyst used in a fluorination reaction such as the production of R125 may have a working life of several months or even a year or more. The catalysts of the invention preferably also have a mechanical strength that enables relatively easy handling, for example they may be charged to reactors or discharged from reactors using known techniques.

The catalysts of the invention may be provided in any suitable form known in the art. For example, they may be provided in the form of pellets or granules of appropriate size for use in a fixed bed or a fluidised bed. The catalysts may be supported or unsupported. If the catalyst is supported, suitable supports include $AlF_3$, fluorinated alumina or activated carbon.

The present invention also provides methods for producing the catalysts of the invention.

Suitable methods include the heat treatment of an amorphous catalyst precursor. The amorphous catalyst precursors can be obtained by any method known in the art for producing amorphous chromia-based catalysts. Suitable methods include co-precipitation, for example from a solution of a nitrate of the additional metal or metals and a solution of chromium nitrate on the addition of ammonium hydroxide; for example by co-precipitation from solutions of zinc and chromium nitrates on the addition of ammonium hydroxide. Alternatively, surface impregnation of the additional metal or metals or a compound thereof onto an amorphous chromia catalyst can be used.

Further methods for preparing the amorphous catalyst precursor include, for example, reduction of a chromium (VI) compound, for example a chromate, dichromate, in particular ammonium dichromate, to chromium (III), by the additional metal (eg zinc metal), followed by co-precipitation and washing; or mixing as solids, a chromium (VI) compound and an oxidisable additional metal compound, for example zinc acetate or zinc oxalate, and heating the mixture to high temperature in order to effect reduction of the chromium (VI) compound to chromium (III) oxide and the additional metal salt to an oxide.

The additional metal may be introduced into and/or onto the amorphous catalyst precursor in the form of a compound, for example a halide, oxyhalide, oxide or hydroxide depending at least to some extent upon the catalyst preparation technique employed. In the case where amorphous catalyst precursor preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of the additional metal and chromium may be co-precipitated (for example by the use of a base such as sodium hydroxide or ammonium hydroxide) and then converted to the oxides to prepare the amorphous catalyst precursor, for example an amorphous catalyst precursor comprising a mixed oxide of zinc and chromium. Mixing and milling of an insoluble additional metal compound with the basic amorphous catalyst precursor provides a further method of preparing the amorphous catalyst precursor. A method for making amorphous catalyst precursor based on chromium oxyhalide comprises adding a compound of the additional metal to hydrated chromium halide.

The amount of additional metal introduced to the amorphous catalyst precursor depends upon the preparation method employed. It is believed that the working catalyst has a surface containing cations of the additional metal located in a chromium-containing lattice, for example chromium oxide, oxyhalide, or halide lattice. Thus the amount of the additional metal required is generally lower for catalysts made by impregnation than for catalysts made by other methods such as co-precipitation, which also contain the additional metal in non-surface locations.

Any of the aforementioned methods, or other methods, may be employed for the preparation of the amorphous catalyst precursors used to produce the catalysts of the present invention.

Fluorination catalysts are typically stabilised by heat treatment before use such that they are stable under the environmental conditions that they are exposed to in use. This stabilisation is often a two-stage process. In the first stage, the catalyst is stabilised by heat treatment in nitrogen or a nitrogen/air environment. In the art, this stage is often called "calcination". Fluorination catalysts are then typically stabilised to hydrogen fluoride by heat treatment in hydrogen fluoride. This stage is often termed "pre-fluorination".

The present inventors have found that by careful control of the conditions under which these two heat treatment stages are conducted crystallinity can be induced into the catalyst to a controlled degree.

For example, an amorphous catalyst precursor may be heat treated at a temperature of from about 300 to about 600° C., preferably from about 400 to 600° C., more preferably from 500 to 590° C., for example 520, 540, 560 or 580° C. for a period of from about 1 to about 12 hours, preferably for from about 2 to about 8 hours, for example about 4 hours in a suitable atmosphere. Suitable atmospheres under which this heat treatment can be conducted include an atmosphere of nitrogen or an atmosphere having an oxygen level of from about 0.1 to about 10% v/v in nitrogen. Other oxidizing environments could alternatives be used. For example, environments containing suitable oxidizing agents include, but are not limited to, those containing a source of nitrate, $CrO_3$ or $O_2$ (for example air). This heat treatment stage can be conducted in addition to or instead of the calcining stage that is typically used in the prior art to produce amorphous catalysts.

Conditions for the pre-fluorination stage can be selected so that they induce a change in the crystallinity of the catalyst or so that they do not induce such a change. The present inventors have found that heat treatment of the catalyst precursor at a temperature of from about 250 to about 500° C., preferably from about 300 to about 400° C. at atmospheric or superatmospheric pressure for a period of from about 1 to about 16 hours in the presence of hydrogen fluoride, optionally in the presence of another gas such as air, can produce a catalyst in which the crystallinity is as defined above, for example from 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

The pre-fluorination treatment typically has the effect of lowering the surface area of the catalyst. After the pre-fluorination treatment the catalysts of the invention typically have a surface area of 50 to 200 m²/g for example less than about 100 m²/g.

Conditions can be selected such that one or both of these heat treatment stages induce crystallinity in the catalyst within the ranges defined above, for example so that 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

Particularly preferred catalysts of the invention are those which contain from 1 to 10% by weight of zinc, for example 4, 6 or 8% by weight of zinc and have a degree of crystallinity of 0.8 to 2.6% by weight of the catalyst, for example about 1.0% by weight. Such catalysts can be prepared by heat treatment of an amorphous catalyst as described above, preferably at a temperature of from 500 to 600° C., for example at 520 to 580° C. in for example a nitrogen atmosphere. The amorphous catalyst is preferably prepared by a co-precipitation method as described above.

In use, the catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst.

As used herein, by the term "amorphous" we mean a material such as a catalyst or catalyst precursor that has a degree of crystallinity of less than 0.1% by weight of the catalyst or catalyst precursor.

The present invention also provides a process for producing a fluorinated hydrocarbon, which comprises reacting a halogenated hydrocarbon with hydrogen fluoride in the presence of a catalyst of the invention.

The catalysts of the invention may be used in any fluorination reaction in which chromia-based catalysts may be employed. The catalysts are particularly suited for use in the reaction of halogenated hydrocarbons, particularly chlorine-containing hydrocarbons with hydrogen fluoride. Such reactions have been extensively reported in the prior art and will be familiar to the person of ordinary skill in the art. Reactions in which the catalysts of the invention may be used include, but are not limited to, the fluorination of halogenated aliphatic hydrocarbons containing from 1 to 6 carbon atoms. For example, the fluorination of methylene chloride to produce difluoromethane (R32), trichloroethylene to produce 1,1,1,2-trifluoro-2,2-dichloroethane (R133a) and 1,1,1,2-tetrafluoroethane (R134a), R133a to produce R134a, perchloroethylene to produce pentafluoroethane (R125), chlorotetrafluoroethanes (R124, R124a) and dichlorotrifluoroethanes (R123, R123a, R123b), R123 to produce R124 and R125, R124 to produce R125 and 1,1,2,2-tetrachloroethane to produce R134.

The catalysts of the present invention are particularly useful in processes for the production of R134a and R125.

The fluorination reactions can be conducted under the conditions described in the prior art. For example, the fluorination reactions can take place in the liquid or vapour phase, although the use of the vapour phase is preferred. The conditions such as temperature, pressure, ratios of reactants and the number of reaction steps for carrying out fluorination reactions using chrormia-based catalysts are well known in the art and are generally applicable to reactions using the catalysts of the present invention.

The catalysts of the invention can be used in a process for the preparation of 1,1,1,2-tetrafluoroethane, which comprises reacting 1-chloro-2,2,2-trifluoroethane with hydrogen fluoride in the vapour phase in the presence of the catalyst of the invention. This process may be carried out under atmospheric or superatmospheric pressure at a temperature of from about 250° C. to 500° C.

1-Chloro-2,2,2-trifluoroethane can be obtained by reacting trichloroethylene with hydrogen fluoride in the vapour-phase in the presence of a catalyst of the present invention. Typical reaction conditions for this reaction are atmospheric or superatmospheric pressure and a temperature in the range of about 180° C. to about 300° C.

The production of 1,1,1,2-tetrafluoroethane from 1-chloro-2,2,2-trifluoroethane results in a product stream containing the toxic impurity 1-chloro-2,2,-difluoroethylene. This impurity can be removed by reacting it with hydrogen fluoride in the vapour phase in the presence of a chromium containing catalyst at a temperature below about 270° C., for example 50° C. to 270° C. The catalysts of the invention may be employed in this reaction.

The catalysts of the invention can be used in a process for the production of pentafluoroethane. One such process comprises (i) contacting perchloroethylene with hydrogen fluoride in the vapour phase in the presence of a catalyst of the invention to form a product stream comprising a hydrochlorofluoroethane of formula $C_2HCl_{1+x}F_{1+y}$, wherein x and y are each independently 0, 1, 2 or 3 provided that x+y is 3, and (ii) contacting the product from step (i) with hydrogen fluoride in the vapour phase and in the presence of a catalyst of the invention to produce pentafluoroethane. Preferably the same catalyst is used in steps (i) and (ii).

Steps (i) and (ii) of the process may be conducted in a single reaction vessel, for example in different reaction zones of the same reactor vessel, or they may be carried out in separate reaction vessels. By a "reaction zone" there is meant a zone or region under certain conditions of temperature and pressure and by different reaction zones there is meant zones or regions at different temperatures.

The process is preferably operated on a continuous basis in which perchloroethylene and hydrogen fluoride are fed to step (i) and additional hydrogen fluoride, if required is fed to step (ii).

The product stream from step (ii) may purified so as to recover pentafluoroethane. Any unreacted hydrochlorofluoroethanes of formula $C_2HCl_{1+x}F_{1+y}$ may be recycled to step (i) or step (ii) of the process.

The product stream from step (ii) may be passed over a fluorination catalyst heated to low temperatures, for example a temperature of from about 80° C. to about 200° C. in order to convert any unsaturated impurities present to saturated hydrochlorofluoroethanes, which may be recycled to step (i) or (ii) of the process.

When the fluorination reactions are carried in two or more separate reaction vessels, then the reaction vessels may be arranged in parallel or in series.

The catalysts of the invention may provide improved selectivity compared with known catalysts such that the production of undesirable by-products such as R-115 in the production of R-125 is reduced.

The catalysts of the invention may also reduce the production of redox by-products. For example, the production of R143a, R123, R124 and R125 in reactions for the production of R134a can be reduced and the production of R114 and R115 can be reduced in reactions for the production of R125.

The invention is illustrated by the following non-limiting Examples.

Catalyst Preparation Method

The catalysts were made by the calcination of mixtures of zinc and chromium hydroxides made by co-precipitation from solutions of zinc and chromium nitrates on the addition of ammonium hydroxide.

The equipment employed comprised a cooled and stirred 300 ml precipitation tank, which was fed with a stream comprising a mixture of zinc and chromium nitrates and secondly with a stream of ammonium hydroxide. The tank stirrer was rotated at 500 rpm during a catalyst preparation and used a conventional design to achieve effective mixing in the precipitation tank. The mixed-nitrates feed and ammonium hydroxide feed were injected continuously into this tank, at a point close to the stirrer blade to ensure rapid mixing. The mixed-hydroxide product formed in the precipitation tank was collected at an overflow point, which maintained a constant slurry volume of approximately 200 ml in the precipitation tank during a catalyst preparation. The vessel walls were cooled to maintain the precipitation temperature at 14-15° C. and the ammonium hydroxide pumping rate to the vessel finely adjusted to maintain the slurry pH in the range of 7-7.5. A 12.5% w/w ammonia solution in deionised water was used as the base feed in the preparations. The mixed metal nitrate solution had chromium content of approximately 10% w/w plus the relevant zinc content, which was required in the finished catalyst formulation.

400 ml batches of slurry from the precipitator were filtered to recover the co-precipitated hydroxides, which were then washed and filtered a further four times. Here the filter cake was washed by reslurrying in approximately 300 ml of dilute ammonia solution, prepared by adding 2.4 g of the feed 12.5% w/w ammonia solution to 300 ml of deionised water. The batches of washed solid were then dried at 100° C. overnight in a nitrogen atmosphere.

The dried cake was powdered to pass through a 0.5 mm sieve and mixed with 2% w/w graphite. 2-3 g batches of this lubricated powder were then pressed into 13 mm diameter discs using an applied pressure of 5 tes. The compacted hydroxide discs were then crushed and sieved to generate particles in the size range 0.5-1.4 mm for calcination and subsequent catalyst testing.

Catalyst Calcination Method 6 g batches of the compacted and granulated hydroxide were charged into a ½" diameter calcination tube and purged with 60 ml/min of nitrogen. Then the catalyst was calcined by heating to 300° C. for a period of four hours and finally cooled under nitrogen to room temperature, to generate the finished catalyst for performance testing.

Controlled Crystallisation of Catalyst

The catalyst prepared above was further thermally processed at a range of temperatures using 6 g batches of compacted hydroxide to generate levels of crystallinity for further testing. Using this methodology, the crystal structure of the calcined catalyst was adjusted from an initial XRD amorphous structure to a progressively more crystalline composition, as the processing temperature was increased.

Catalyst Test Samples

The above method was followed to prepare catalysts with a mixed oxide formulation $ZnO.Cr_2O_3$ having a Zn content of 4% w/w Zn. The reference catalyst received a single calcination at a temperature of 300° C., which generated a fully amorphous base case catalyst. Then using processing temperatures of 520, 540 and 560° C., three catalyst examples were prepared containing progressively higher contents of crystalline chromium oxide.

The crystalline chromium oxide content of the catalysts were determined using XRD analysis. The equipment was calibrated using amorphous catalyst doped with exact levels of a fully crystalline chromia reference material (NBS (National Bureau of Standards) Standard Reference Material 674 XRD Intensity Chromia).

The catalyst calcined at 300° C. was found to have no detectable crystalline chromia reflections, whereas the materials heat treated at 520, 540 and 560° C. had chromia (012) reflections at 24.48 degrees 2 theta, indicating crystalline chromia contents of 1.0%, 2.6% and 11.5% w/w respectively.

These four materials were then evaluated as catalysts for the fluorination of perchloroethylene.

Catalyst Testing Method and Results

The catalysts were tested to measure their initial activity and selectivity in catalysing the fluorination of perchloroethylene and then were tested for relative stability, when exposed to high temperature HF. The testing methodology was as follows:

A 2 g charge of catalyst particles having a size range of from 0.5 to 1.4 mm was placed in an inconel reactor and purged with a nitrogen flow of 120 ml/min. The catalyst was then dried in the nitrogen stream by heating to 250° C. for a period of 30 minutes. The catalyst was then conditioned in HF by firstly adding a HF flow of 15 ml/min to the diluent nitrogen and conditioning the catalyst for a period of 90 minutes at 250° C. Then the diluent nitrogen flow was reduced to a 2.5 ml/min and the catalyst was heated to 380° C. at a rate of 40° C. per hour. The catalyst was fluorinated at 380° C. under these HF flow conditions for an additional period of 16 hours. Then the HF stabilised catalyst was cooled to 350° C. and a 1 ml/min flow of perchloroethylene in 5 ml/min flow of nitrogen were added to the feed, to generate a reactor feed ratio of Per:HF:N2 of 1:15:7.5 ml/min.

After the perchloroethylene fluorination reaction had been carried-out for approximately two hours at 350° C., the observed catalyst performance stabilised. Then the reactor temperature was adjusted to identify the perchloroethylene fluorination catalyst temperature, which gave a 30% conversion of the perchloroethylene feed. More active catalysts were able to deliver the target 30% perchloroethylene conversion at a lower reaction temperature.

Useful perchloroethylene fluorination reaction products include 122, 123, 124, 125 and 1111, however the reaction also generates the unwanted by-products 133a, 134a, 114 and 115, and which cause losses in feed conversion efficiency and furthermore cause additional product purification difficulties and costs.

In the evaluation of the amorphous base case 1 catalyst, which contained 4% Zn and had been calcined at 300° C., the reaction temperature required to achieve a 30% perchloroethylene conversion was 348° C. and under these conditions 6.54% of the reaction products were the unwanted compounds 133a, 134a, 114 plus 115.

After the initial activity study, the base case catalyst's stability was evaluated by exposing the catalyst to high temperature HF. This study was performed by heating the catalyst in a HF flow of 15 ml/min diluted with 2.5 ml/min of nitrogen for 16 hours at 480° C. and then by cooling the catalyst to 350° C. to repeat the perchloroethylene fluorination study. Finally, the catalyst was stressed further by heating in HF to 500° C. for 16 hours and the catalyst's performance was re-measured. The results are tabulated below and indicate that the catalyst's activity increased in the first high temperature HF treatment but then the catalyst deactivated, when heated at the higher HF treatment temperature of 500° C. These results were reflected in the operating temperature required to achieve a standard 30% perchloroethylene conversion, which changed from 348° C. to 313° C. and then to 337° C., when using the above testing procedure.

The loss of selectivity caused by the formation of unwanted by-products at the standard 30% perchloroethylene conversion was observed to decrease from 6.54% to 3.37% after heating to 480° C. in HF, but after HF stressing to 500° C., increased again to 4.83%. These results form the reference base case 1 data for the amorphous 4% Zn containing chromium oxide catalyst.

EXAMPLE 1

A mixture of zinc and chromium hydroxides made using the catalyst preparation method described above and containing 4% by weight zinc was further thermally processed by heating in nitrogen for 4 hours at 520° C. The resultant material contained 1.0% w/w crystalline chromium oxide.

Using a 2 g charge of this catalyst, the methodology used in the base case study was repeated to give a data set for this partially crystalline catalyst. The results are presented in the summary Tables below and demonstrate that the partial crystallisation of the catalyst had induced a great increase in activity, allowing it to achieve a 30% perchloroethylene conversion at only 227° C. with only a 0.26% loss of selectivity to 133a, 134a, 114 and 115 by-products.

As with the base case example, the partially crystallised catalyst was observed to activate on heating in HF to 480° C., reducing the operating temperature to 212° C., however little deactivation was observed after stressing the catalyst at 500° C. in HF. The by-product levels remained low after the catalyst had been stressed in HF.

EXAMPLE 2

A mixture of zinc and chromium hydroxides made using the catalyst preparation method described above and containing 4% by weight zinc was further thermally process in nitrogen for 4 hours at 540° C. The resultant material contained 2.6% w/w crystalline chromium oxide.

A 2 g charge of this catalyst was tested before and after HF stressing, following the methodology described above and the results of these studies are compared with those obtained for the base case and Example 1 catalyst in the following Tables.

This 2.6% crystalline chromia content catalyst was found to have a lower peak activity than the 1.0% crystalline catalyst, having a minimum operating temperature of 217° C. rather than 212° C. The catalyst ageing rate and by-product levels were also found to be slightly higher that observed for the 1.0% crystalline catalysts, but still far superior to the amorphous base case Example.

EXAMPLE 3

A mixture of zinc and chromium hydroxides made using the catalyst preparation method described above and containing 4% by weight zinc was further processed in nitrogen for 4 hours at 560° C. The processed catalyst contained 11.5% w/w crystalline chromium oxide. Using the methodology described above, this catalyst proved less active and less selective than the catalysts of Examples 1 and 2, but superior to the amorphous base case catalyst.

The lowest reaction temperature required to deliver a 30% perchloroethylene conversion was 233° C., which was 21° C. above that required by the 1.0% crystalline catalyst and the by-product levels were approximately four times higher.

TABLE 1

4% Zinc promoted Chromium oxide Catalyst
Measurement of Catalyst Perchloroethylene Fluorination Activity
(Temperature Required to Convert 30% of the Perchloroethylene Fed)

| Catalyst | Calcination Temperature Deg. C. | % Cryst $Cr_2O_3$ Content | High Temperature HF Treatment Temperature Deg. C. | | |
|---|---|---|---|---|---|
| | | | 380 | 480 | 500 |
| Basecase 1 | 300 | 0.0 | 348 | 313 | 337 |
| Ex. 1 | 520 | 1.0 | 227 | 212 | 228 |
| Ex. 2 | 540 | 2.6 | 220 | 217 | 235 |
| Ex. 3 | 560 | 11.5 | 246 | 233 | 291 |

TABLE 2

4% Zinc promoted Chromium oxide Catalyst
Measurement of unwanted By-product Levels
(% Loss of Selectivity to Byproducts at 30% Per Conversion)

| Catalyst | Calcination Temperature Deg. C. | % Cryst $Cr_2O_3$ Content | High Temperature Treatment Temperature Deg. C. | | |
|---|---|---|---|---|---|
| | | | 380 | 480 | 500 |
| Basecase 1 | 300 | 0.0 | 6.54 | 3.37 | 4.83 |
| Ex. 1 | 520 | 1.0 | 0.26 | 0.13 | 0.23 |
| Ex. 2 | 540 | 2.6 | 0.14 | 0.24 | 0.41 |
| Ex. 3 | 560 | 11.5 | 1.01 | 0.55 | 1.12 |

EXAMPLE 4

The methodology described above and used in Examples 1 to 3 was repeated using a mixture of zinc and chromium hydroxides made using the catalyst preparation method described above and containing 6% by weight zinc and thermally processed by heating in nitrogen for 4 hours at 520, 540, 560, 580 and 600° C.

TABLE 3

6% Zinc promoted Chromium oxide Catalyst
Measurement of Catalyst Perchloroethylene Fluorination Activity
(Temperature Required to Convert 30% of the Perchloroethylene Fed)

| Catalyst | Calcination Temperature Deg. C. | % Cryst $Cr_2O_3$ Content | High Temperature HF Treatment Temperature Deg. C. | | |
|---|---|---|---|---|---|
| | | | 380 | 480 | 500 |
| Basecase 1 | 300 | 0.0 | 256 | 272 | 325 |
| 1 | 520 | 0.7 | 226 | 220 | 235 |
| 2 | 540 | 1.0 | 223 | 218 | 232 |
| 3 | 560 | 2.6 | 219 | 218 | 238 |
| 4 | 580 | 5.2 | 224 | 235 | 285 |
| 5 | 600 | >10 | 234 | 299 | — |

TABLE 4

6% Zinc promoted Chromium oxide Catalyst
Measurement of unwanted By-product Levels
(% Loss of Selectivity to Byproducts at 30% Per Conversion)

| Catalyst | Calcination Temperature Deg. C. | % Cryst $Cr_2O_3$ Content | High Temperature Treatment Temperature Deg. C. | | |
|---|---|---|---|---|---|
| | | | 380 | 480 | 500 |
| Basecase 1 | 300 | 0.0 | 0.578 | 0.645 | 2.191 |
| 1 | 520 | 0.7 | 0.254 | 0.236 | 0.378 |
| 2 | 540 | 1.0 | 0.231 | 0.216 | 0.283 |
| 3 | 560 | 2.6 | 0.267 | 0.236 | 0.343 |
| 4 | 580 | 5.2 | 0.284 | 0.333 | 1.015 |
| 5 | 600 | >10 | 0.336 | 1.146 | — |

EXAMPLE 5

The methodology described above and used in Examples 1 to 3 was repeated using a mixture of zinc and chromium hydroxides made using the catalyst preparation method described above and containing 8% by weight zinc and thermally processed by heating in nitrogen for 4 hours at 540, 560, 580, 600 and 620° C.

TABLE 5

8% Zinc promoted Chromium oxide Catalyst
Measurement of Catalyst Perchloroethylene Fluorination Activity
(Temperature Required to Convert 30% of the Perchloroethylene Fed)

| Catalyst | Calcination Temperature Deg. C. | % Cryst $Cr_2O_3$ Content | High Temperature HF Treatment Temperature Deg. C. | | |
|---|---|---|---|---|---|
| | | | 380 | 480 | 500 |
| Basecase 1 | 300 | 0.0 | 325 | — | — |
| 1 | 540 | 1.0 | 229 | 237 | 265 |
| 2 | 560 | 3.0 | 237 | 237 | 257 |
| 3 | 580 | 4.0 | 227 | 240 | 263 |
| 4 | 600 | 6.0 | 232 | 242 | 276 |
| 5 | 620 | 10 | 236 | 259 | 345 |

TABLE 6

8% Zinc promoted Chromium oxide Catalyst
Measurement of unwanted By-product Levels
(% Loss of Selectivity to Byproducts at 30% Per Conversion)

| Catalyst | Calcination Temperature Deg. C. | % Cryst $Cr_2O_3$ Content | High Temperature Treatment Temperature Deg. C. | | |
|---|---|---|---|---|---|
| | | | 380 | 480 | 500 |
| Basecase 1 | 300 | 0.0 | 3.57 | — | — |
| 1 | 540 | 1.0 | 1.151 | 0.447 | 0.829 |
| 2 | 560 | 3.0 | 0.528 | 0.381 | 0.628 |
| 3 | 580 | 4.0 | 0.298 | 0.422 | 0.650 |
| 4 | 600 | 6.0 | 0.353 | 0.472 | 0.819 |
| 5 | 620 | 10 | 0.393 | 0.570 | 3.466 |

EXAMPLE 6

The methodology described above and used in Examples 1 to 3 was repeated using a mixture of zinc and chromium hydroxides made using the catalyst preparation method described above and containing 10% by weight zinc and thermally processed by heating in nitrogen for 4 hours at 600° C.

TABLE 7

10% Zinc promoted Chromium oxide Catalyst
Measurement of Catalyst Perchloroethylene Fluorination Activity
(Temperature Required to Convert 30% of the Perchloroethylene Fed)

| Catalyst | Calcination Temperature Deg. C. | % Cryst $Cr_2O_3$ Content | High Temperature HF Treatment Temperature Deg. C. | | |
|---|---|---|---|---|---|
| | | | 380 | 480 | 500 |
| Basecase 1 | 300 | 0.0 | 352 | — | — |
| 1 | 600 | 1.0 | 239 | 258 | 297 |

TABLE 8

10% Zinc promoted Chromium oxide Catalyst
Measurement of unwanted By-product Levels
(% Loss of Selectivity to Byproducts at 30% Per Conversion)

| Catalyst | Calcination Temperature Deg. C. | % Cryst $Cr_2O_3$ Content | High Temperature Treatment Temperature Deg. C. | | |
|---|---|---|---|---|---|
| | | | 380 | 480 | 500 |
| Basecase 1 | 300 | 0.0 | 4.365 | — | — |
| 1 | 600 | 1.0 | 0.567 | 0.580 | 0.969 |

The procedure described above for testing the properties of the catalysts in the fluorination of perchloroethylene was repeated except that perchloroethylene was replaced by R123 and the target was 50% conversion of the R123 fed.

TABLE 9

10% Zinc promoted Chromium oxide Catalyst
Measurement of Catalyst R123 Fluorination Activity
(Temperature Required to Convert 50% of the R123 Fed)

| Catalyst | Calcination Temperature Deg. C. | % Cryst $Cr_2O_3$ Content | High Temperature HF Treatment Temperature Deg. C. | | |
|---|---|---|---|---|---|
| | | | 380 | 480 | 500 |
| Basecase 1 | 300 | 0.0 | 329 | — | — |
| 1 | 600 | 1.0 | 288 | 307 | 336 |

In all of the above Tables "–" indicates that it was not possible to obtain the target.

EXAMPLE 7

An amorphous catalyst comprising 6% Zn and a catalyst having a degree of crystallinity of 1% and containing 6% Zn (obtained as described in Example 4) were used in a process for the production of HFC-134a from trichloroethylene and hydrogen fluoride at a fixed residence time of about 1.3 seconds.

| % Cryst $Cr_2O_3$ Content | Catalyst ageing temperature (° C.) | | | |
|---|---|---|---|---|
| | 460 | 500 | 519 | 527 |
| 0 | 293.9 | 300.3 | 311.1 | 354.6 |
| 1 | 287.4 | 288.7 | 293.8 | 324.7 |

The catalyst comprising 1% crystalline chromia was both more active and more stable than amorphous material as evidenced by lower temperatures required for 10% yield at all ageing conditions.

EXAMPLE 8

The interaction between calcination temperature, time and atmosphere and their effect on the crystallization of a 6% Zn/chromia catalyst was studied and statistical modeling methods were used to illustrate how the calcinations conditions can be used to induce varying levels of crystallinity as required.

A series of experiments were performed in which 8 g samples of a 6% Zn/chromia catalyst were subjected to calcination across a range of conditions and the level of crystallinity induced determined by X-Ray diffraction:

| Calcination Time (t, hrs) | Calcination Temperature (T, ° C.) | Atmosphere nitrogen:air (D, v/v) | % Cryst $Cr_2O_3$ Content |
|---|---|---|---|
| 4 | 400.0 | 15 | 1 |
| 4 | 400.0 | 15 | 1 |
| 2 | 450.0 | 20 | 9 |
| 6 | 350.0 | 20 | 0 |
| 2 | 450.0 | 10 | 18 |
| 2 | 350.0 | 10 | 0 |
| 6 | 450.0 | 20 | 20 |
| 6 | 350.0 | 10 | 0 |
| 6 | 450.0 | 10 | 30 |
| 4 | 400.0 | 15 | 1 |
| 2 | 350.0 | 20 | 0 |

Statistical modeling methods were used to generate a polynomial function that could be used to predict the crystallinity level induced in the catalyst given t,T and D. It was found that crystallinity could be predicted using the following polynomial:

$$X_{st}(\%) = -71.75 - 11.37*Time + 0.2050*Temperature + 0.975*Dilution + 0.03250*Time*Temperature + 0.087501*Time*Dilution - 0.008500*Temperature*Dilution - 0.0002500*Time*Temperature*Dilution$$

The following list illustrates how this polynomial can be used to identify possible solutions of this equation in which the predicted level of chromia crystallinity induced would <4% i.e. in the optimum range:

| Number | Time (hrs) | Temperature (° C.) | Dilution (air:nitrogen v/v) |
|---|---|---|---|
| 1 | 4.000 | 436.5 | 13.86 |
| 2 | 4.000 | 446.9 | 19.98 |
| 3 | 4.000 | 440.4 | 10.45 |
| 4 | 4.000 | 356.1 | 17.72 |
| 5 | 4.000 | 391.8 | 16.42 |
| 6 | 4.000 | 382.1 | 14.32 |
| 7 | 4.000 | 444.9 | 12.35 |
| 8 | 4.000 | 380.1 | 10.22 |
| 9 | 4.000 | 444.6 | 19.20 |
| 10 | 4.000 | 426.6 | 10.67 |

The invention claimed is:

1. A chromia-based fluorination catalyst comprising from 6% to 25% by weight of at least one additional metal selected Iron zinc, nickel, aluminium and magnesium in which from 0.5 to 2.5% by weight of the catalyst is in the form of one or more crystalline compounds of chromium.

2. A catalyst according to claim 1, wherein the additional metal is zinc.

3. A catalyst according to claim 1 having a surface area of at least 50 m²/g.

4. A catalyst according to claim 3 having a surface area of from 70 to 250 m²/g.

5. A canal according to claim 1 having a sulphate content of less 10% w/w.

6. A method for producing a catalyst as defined claim 1, which method comprises heat treating an amorphous catalyst precursor at a temperature of from about 300 to about 600° C. for a period of from about 1 to about 12 hours in an atmosphere of nitrogen or an atmosphere having an oxygen level of from about 0.1 to about 10% v/v in nitrogen.

7. A method for producing a catalyst as defined in claim 1, which method comprises heat treating an amorphous catalyst precursor at a temperature of from about 250 to about 500° C. for a period of from about 1 to about 16 hours at atmospheric or superatmospheric pressure in the presence of hydrogen fluoride.

8. A process for producing a fluorinated hydrocarbon, which process comprises reacting a halogenated hydrocarbon with hydrogen fluoride in the presence of a catalyst as defined in claim 1.

9. A process according to claim 8 that is carried out at elevated temperature in the vapour phase.

10. A process according to claim 9 for the production of 1,1,1,2-tetrafluoroethane or pentafluoroethane.

\* \* \* \* \*

UNITED STATES PATENT AND TRADEMARK OFFICE
CERTIFICATE OF CORRECTION

PATENT NO.        : 9,771,309 B2
APPLICATION NO.   : 11/887972
DATED             : September 26, 2017
INVENTOR(S)       : Andrew P. Sharratt and John D. Scott It is certified that error appears in the above-identified patent and that said Letters Patent is hereby corrected as shown below:

In the Claims

Column 14, Lines 24-28 Claim 1:
"1. A chromia-based fluorination catalyst comprising from 6% to 25% by weight of at least one additional metal selected Iron zinc, nickel, aluminum and magnesium in which from 0.5 to 2.5% by weight of the catalyst is in the form of one or more crystaline compounds of chromium." should read --1. A chromia-based fluorination catalyst comprising from 6% to 25% by weight of at least one additional metal selected from zinc, nickel, aluminum and magnesium in which from 0.5 to 2.5% by weight of the catalyst is in the form of one or more crystaline compounds of chromium.--

Signed and Sealed this
Sixth Day of February, 2018

Joseph Matal
*Performing the Functions and Duties of the*
*Under Secretary of Commerce for Intellectual Property and*
*Director of the United States Patent and Trademark Office*